US008845892B2

(12) United States Patent
Benevides et al.

(10) Patent No.: US 8,845,892 B2
(45) Date of Patent: Sep. 30, 2014

(54) DEVICE, METHOD AND APPARATUS FOR PERFORMING SEPARATIONS

(75) Inventors: Christopher C. Benevides, Tiverton, RI (US); Jonathan L. Belanger, Whitinsville, MA (US); Marianna Kele, Milford, MA (US); Thomas H. Walter, Ashland, MA (US); Raymond P. Fisk, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 330 days.

(21) Appl. No.: 11/573,314

(22) PCT Filed: Aug. 17, 2005

(86) PCT No.: PCT/US2005/029203
§ 371 (c)(1),
(2), (4) Date: Jan. 10, 2008

(87) PCT Pub. No.: WO2006/023524
PCT Pub. Date: Mar. 2, 2006

(65) Prior Publication Data
US 2008/0257835 A1 Oct. 23, 2008

Related U.S. Application Data

(60) Provisional application No. 60/602,795, filed on Aug. 19, 2004.

(51) Int. Cl.
| | |
|---|---|
| B01D 15/08 | (2006.01) |
| G01N 30/60 | (2006.01) |
| G01N 30/14 | (2006.01) |
| B01D 15/12 | (2006.01) |
| B01D 15/22 | (2006.01) |
| B01J 20/10 | (2006.01) |
| G01N 30/32 | (2006.01) |

(52) U.S. Cl.
CPC .............. *B01D 15/125* (2013.01); *G01N 30/14* (2013.01); *G01N 2030/322* (2013.01); *B01D 15/22* (2013.01)
USPC .................. 210/198.2; 210/656; 73/61.53

(58) Field of Classification Search
USPC .............................................. 210/198.2, 656
See application file for complete search history.

(56) References Cited

U.S. PATENT DOCUMENTS

| | | | |
|---|---|---|---|
| 3,763,879 A | 10/1973 | Jaworek | |
| 4,313,828 A * | 2/1982 | Brownlee | ................... 210/198.2 |

(Continued)

FOREIGN PATENT DOCUMENTS

| | | |
|---|---|---|
| JP | 3-8759 A | 1/1991 |
| JP | 09-072890 A | 3/1997 |

(Continued)

OTHER PUBLICATIONS

Office Action for corresponding Chinese Patent Application No. 2007-527962 dated Dec. 21, 2010 (8 pages).

(Continued)

*Primary Examiner* — Katherine Zalasky
(74) *Attorney, Agent, or Firm* — Schmeiser, Olson & Watts LLP

(57) ABSTRACT

Embodiments of the present invention are directed to devices, methods and apparatus for performing separations in which particulates are separated or removed from a fluid stream flowing to a column. In one embodiment directed to a device, the invention includes a body (13) having a first surface (17) and a second surface (19) and at least one wall (23). At least one of the first surface (17) and second surface (19) is for receiving in sealing engagement a first conduit means. The remaining first surface (17) or second surface (19) is for engaging a column or a second conduit (19). The at least one wall (23) extends between the first surface (17) and the second surface (19). The body (13) has at least one opening (25) extending from the first surface (17) to the second surface (19) defining a chamber for receiving a solid phase separation media assembly (15). The device further includes a solid phase separation media assembly (15) within the chamber formed in the opening of the body between the first surface (17) and the second surface (19). The solid phase separation media assembly (15) is for removing particulates and undesired materials of a fluid flowing through the chamber. The body is constructed and arranged to fit in a body fitting to be attached to a column or which body fitting is part of an assembly for communicating with an column or a detector.

38 Claims, 7 Drawing Sheets

(56) References Cited

U.S. PATENT DOCUMENTS

| | | | |
|---|---|---|---|
| 4,451,364 A * | 5/1984 | Higgins et al. | 210/198.2 |
| 4,522,715 A * | 6/1985 | Walters | 210/198.2 |
| 4,551,249 A * | 11/1985 | Shackelford et al. | 210/198.2 |
| 4,710,289 A * | 12/1987 | Wermuth et al. | 210/198.2 |
| 5,472,598 A * | 12/1995 | Schick | 210/198.2 |
| 5,736,036 A * | 4/1998 | Upchurch et al. | 210/198.2 |
| 6,139,733 A | 10/2000 | Hargro et al. | |
| 6,361,687 B1 * | 3/2002 | Ford et al. | 210/198.2 |
| 6,416,663 B1 * | 7/2002 | Miroslav et al. | 210/198.2 |
| 6,679,989 B2 * | 1/2004 | Willis et al. | 210/198.2 |

FOREIGN PATENT DOCUMENTS

| | | |
|---|---|---|
| JP | 2002-523728 | 7/2002 |
| JP | 2002-536651 | 10/2002 |
| WO | 9408685 | 4/1994 |

OTHER PUBLICATIONS

First Examination Report in related Indian patent application No. 979/DELNP/2007, mailed on Nov. 26, 2013; 2 pages.

* cited by examiner

DEVICE, METHOD AND APPARATUS FOR PERFORMING SEPARATIONS

CROSS REFERENCE TO RELATED APPLICATION

This application claims priority from U.S. Provisional Patent Application No. 60/602,795, filed Aug. 19, 2004. The contents of these applications are incorporated herein by reference.

STATEMENT REGARDING FEDERALLY SPONSORED RESEARCH AND DEVELOPMENT

N/A

FIELD OF THE INVENTION

The present invention relates to devices, methods and apparatus for performing separations, and, in particular, separations performed by chromatography for analytical purposes.

BACKGROUND OF THE INVENTION

The present invention relates to devices, methods and apparatus for performing chemical separations, and, in particular, for performing chromatography. The term "chromatography" refers to the separation of compounds based on differences in affinity or absorbance. In chromatography, compounds are held in a solution of a gas, liquid or supercritical fluid. The solution in which the compound is dissolved is known as the "solvent". The dissolved compounds exhibit differences in absorbance or affinity to a media that is not dissolved in the solvent. This media is held in place, stationary to the flow of a solution holding the dissolved compounds. This media is commonly a solid phase material.

Chromatography is a common research tool and can be used to process samples for analysis by various detection techniques. Chromatography can be used to grossly separate many compounds from a sample, as an extraction technique. Chromatography can also be utilized as a fine separation technique in which subtle changes in molecular structure and function alter the affinity of the compounds to an immobilized media. Closely related compounds, for example drugs and drug metabolytes, can be effectively separated.

Chromatography can be performed in open systems or closed systems. In open systems chromatography is performed without significant pressure differentials. Examples of devices used in an open type system are well-like devices, such as ninety-six well extraction plates.

An example of a closed system is high performance or high pressure liquid chromatography (HPLC). Closed chromatography is normally performed with columns and cartridges through which solutions are pumped under pressure. The columns and cartridges typically have a packing of an immobilized media, such as silica or a polymeric particles, to which compounds adsorb. A sample is flowed through the media and compounds in the sample adsorb to the media. This paper will make no distinction between a column and cartridge, and will use the term "column" to mean column or cartridge unless specifically stated otherwise. Analytical columns are columns made with fine tolerances for effecting reproducible qualitative and quantitative separations of closely related compounds. Columns, and analytical columns in particular, are expensive.

The initial flowing of sample on to the media is called "loading". Removing the potential compounds of interest is known as "eluting". Elution is often performed by changing the solvent composition. Preparing the media to receive the sample is known as "conditioning". Ensuring the prior sample is removed from a media, to allow a next sample to be loaded on the media is known as "washing".

The term "sample" will be used to denote any material that is received for processing. In clinical settings, a sample may comprise a biological fluid or tissue. The term "analyte" will be used to mean a composition of interest, potentially present in sample. Samples and solvents may contain particulates, globules and other materials that are not of analytical or diagnostic interest. For simplicity, this paper will refer to all such particulates, globules and materials as particulates. These particulates may accumulate and reduce flow in columns such that the column no longer is useful.

Columns are normally in fluid communication with a detector. As used in this paper, the term "detector" refers to a device that produces a signal in response to the presence or absence of a composition. A typical detector is in the nature of, by way of example, without limitation, mass spectrometers, optical sensors, such ramon detectors, light scattering detectors, fluorescent detectors, chemi-luminescent detectors, light absorbance detectors, light refraction detectors, electrochemical detectors, viscosity detectors, nuclear magnetic resonance detectors.

HPLC is normally performed at pressure of up to 3,000 pounds per square inch (psi). However, there is a desire to operate at pressures above 3,000 psi, including pressures in the ultra pressure region of 4,000 psi up to 15,000 psi. At such elevated pressures and with higher flow rates associated with such pressures, the size of columns and conduits to effect fluid communication between fluidic elements is generally reduced. With the smaller size, columns are more sensitive to particulates and pressure pulsation. A used herein, pressure pulsation refers to the changes in pressure associated with pump, valve and other mechanical inefficiencies and errors.

Guard columns have been used to protect and extend the useful life of analytical However, the use of guard columns to protect other columns, such as an analytical column, often entails substantial additional conduits and tubing. The additional tubing and conduits adds to the potential of leaks and contributes to band spreading due to the effects of the walls of the conduits and tubes, and decreases the responsiveness of the system to change fluids during elution process or washing processes.

Thus, there is a need for devices methods and apparatus which function to protect a column and detector sensitive to the effects of particulates and pressure pulsations and ripples in a high pressure and ultra high-pressure environment.

SUMMARY OF THE INVENTION

Embodiments of the present invention are directed to devices, methods and apparatus for performing separations in which particulates are separated or removed from a fluid stream directed to a column. In one embodiment directed to a device, the invention comprises a body having a first surface and a second surface and at least one wall. At least one of the first surface and second surface is for receiving in sealing engagement a first conduit means. The remaining first surface or second surface is for engaging a column or a second conduit means. The at least one wall extends between the first surface and the second surface. The body has at least one opening extending from the first surface to the second surface defining a chamber for receiving a solid phase separation media assembly. The device further comprises a solid phase separation media assembly within the chamber formed in the opening of the body between the first surface and the second surface. The solid phase separation media assembly is for removing particulates and undesired materials of a fluid flowing through the chamber and to dampen the effects of pressure pulsation. The body is constructed and arranged to fit in a body fitting to be attached to a column, or fit in a column or which body fitting is part of an assembly for communicating with an column or a detector.

Thus, the device separates particulates and undesired material of a fluid prior to the fluid entering a column protecting the column or detector. The device further protects the solid phase media of the column from the effects of pressure ripple and pulsation. The device protects and extends the life of the column. As used herein, extending the life of a column means that the peaks associated with a compound and the relative amount of such compound, in time and magnitude, vary by no more than approximately ten percent.

Columns used in chromatography have an internal diameter. In the event the device is used with a column, preferably, the body has an opening having a diameter sixty to eighty percent of the diameter of the column. For example, in the event the column has an internal diameter of approximately 0.04 to 0.143 inches, the diameter of the body opening is approximately 0.025 to 0.1 inches.

The solid phase separation media assembly is a monolith or a first frit, second frit and a packing of particles or a stacking of frits. Monoliths are formed in situ in the opening with a thickness in a range of 0.2 to 3.0 millimeters. A stacking of frits would have a similar thickness of 0.025 to 0.1 inches.

In the event the solid phase separation media assembly is a first frit, a second frit and a packing of particles of separation material, preferably the first frit fixed to the opening proximal to the first surface of the body. And, similarly, the second frit fixed to the opening proximal to the second surface. The packing is held in opening between the first frit and the second frit, which first and second frit create a chamber. The first frit and second frit and packing of particles are permeable to fluids but substantially impermeable to particulates.

Preferably, the packing of particles has a thickness in a range of 0.2 to 3.0 millimeters. Preferably, the particles have an average diameter of 1 to 5 microns. A preferred first frit and second frit have a porosity of 0.5 microns. A stack of frits, preferably, has a porosity of 0.5 microns.

Preferably, the body has at least one a frit cavity, and more preferably two frit cavities to facilitate placement and securing the first frit and second frit. Each frit cavity comprises a depression in one of first surface and second surface at the opening for receiving a frit.

Preferably, the at least one wall of the body is cylindrical and has an external diameter approximately equal to the external diameter of a column. A typical analytical column has an external diameter of approximately 0.5 mm to 4.0 mm.

Preferably, at least one of the first surface and second surface is capable of deforming in sealing engagement with connectors and columns. However, in the event the body is to rest in the column itself, the diameter of the body is less than the internal diameter of the column. Preferably, the column has a body cavity having a body which it is adjacent.

The body can be made of any material capable of withstanding the pressures at which the device is likely to encounter. Certain high strength plastics, steel, brass, iron, and mixtures thereof are preferred. Preferable, particularly for high and ultra pressure applications, least one of the first surface and surface is softened to facilitate sealing. In the case of bodies formed of metals, the metal forming the first surface and second surface are annealed.

Preferably, the device further comprises a body fitting. The body fitting has a housing having attachment means for sealably engaging at least one of the first surface and second surface to a source of fluid or an intended destination of the fluid. For example, the attachment means may comprise threads which cooperate with threads on columns or connecting means.

One embodiment of the device further comprising a column. The column, preferably has a column abutment surface for sealing engagement with at least one of the first surface and second surface of the body. Preferably, the column abutment surface has a ring projection for focusing compressive forces against the first surface or second surface to which it abuts.

The body fitting housing also has a passage. The passage has an expanded portion, fitting abutment surface and a narrow portion. The expanded portion is sized to receive the body against the fitting abutment surface. The fitting abutment surface sealing engages at least one of the first surface or second surface. The narrow portion of the passage is for transporting said fluid into or out of the opening of the body.

Preferably, the expanded portion is capable of receiving at least one of the ends of a column or a connector. The expanded portion preferably has a hollow having a cylindrical wall, for receiving the body. Preferably, the cylindrical wall also has means for affixing the body fitting to a column or connector. A preferred means for affixing the body fitting to a column or connector is cooperating threads.

Preferably, the narrow portion has means for connecting to tubing. The means for connection to tubing preferably comprises ferrules and associated compression fittings. Thus, the device is capable of being plumbed to receive fluid from a fluid source or to discharge fluid to a further conduit, vessel or apparatus.

In one embodiment the device further comprises a connector. Preferably, the connector is a tube connector having a fluid channel for transporting fluid in or out of the body. The tube connector has a tubular section and a terminal abutment section. The fluid channel extending through the tubular section and the terminal abutment section for transporting fluid into or out of the chamber of the body.

The terminal abutment section has a cylindrical form received within the cylindrical wall of the body fitting for sealing engagement with at least one of first surface or second surface of the body. Preferably, the cylindrical form has an end wall having a planar surface with a ridge to focus compression forces.

Preferably, the expanded section of the passage of the body fitting is capable of receiving a compression fitting assembly for placing the tube connector in fluid communication with other devices, vessels and conduits. One preferred compression fitting assembly comprises a compression piece having a compression piece opening and piece affixing means. The compression piece opening receives the tubular section, allowing the tubular section to extend outward from the piece. The piece affixing means is for affixing the compression piece to the body fitting. A preferred piece affixing means is cooperating threads.

Preferably, the compression fitting assembly further comprises a ferrule. The ferrule is affixed to the tubular section. And, preferably, the compression fitting assembly further comprises a ferrule compression sleeve. The compression sleeve is capable of compressing the ferrule to said tubular section and to the compression sleeve. A preferred compression sleeve has threads whish cooperate with corresponding threads of a compression sleeve receiving fitting.

The devices of the present invention are capable of withstanding internal pressures of greater than about 4,000 psi and up to 15,000 psi.

One embodiment of the present invention features a method of removing particulates and interfering materials from a fluid stream and dampening pressure pulsation and ripple. The method comprises the steps of placing a device in the fluid stream. The device having a body having a first surface and a second surface and at least one wall. At least on of the first surface and second surface is for receiving in sealing engagement a conduit means. And, the remaining first surface and second surface is for engaging a column device or a second conduit means. The wall extends between first surface and the second surface. The body has at least one opening extending from the first surface to the second surface defining a chamber for receiving a solid phase separation media assembly. The device further comprises a solid phase separation media assembly within the chamber formed in the opening of the body between first surface and the second surface. The solid phase separation media assembly is for removing particulates and undesired materials of a fluid flowing through the chamber and dampening the effects of pressure pulsation and ripple. The body is constructed and arranged to fit in a fitting to be attached to a column, or into a column or which fitting is part of a connector, in which the connector is for communicating with a column. The device separates and removes particulates and undesired materials of a fluid prior to said fluid entering a column.

A further embodiment of the present invention is an apparatus for performing separations comprising a pump, conduit means, a column, means for placing a sample in the fluid stream, a body, a body fitting. The pump is for moving fluids to create a fluid stream in suitable conduits and the like. The column is for performing separations. The column is in fluid communication with the pump via conduits to receive the fluid stream. The means for placing a sample in the fluid stream allows the column to separate compounds in the sample as the sample flows through the column. The body has a first surface and a second surface and at least one wall. At least one of the first surface and second surface is for receiving in sealing engagement a conduit means. The remaining first surface or second surface is for engaging a column or a second conduit means. The wall extends between the first surface and second surface, with at least one opening extending from first surface to the second surface defining a chamber for receiving a solid phase separation media assembly. A solid phase separation media assembly is within the chamber formed in the opening of the body between the first surface and the second surface. The solid phase separation media assembly is for removing particulates and undesired components of a fluid flowing through the chamber. The body is constructed and arranged to fit in a body fitting to be attached to an analytical column or which body fitting is part of an assembly for communicating with an column. A body fitting is affixed to the column or interposed in the fluid stream, between the means for placing sample in the fluid stream and the column to extend the operational lifetime of the column.

These and other advantages and features will be apparent to those skilled in the art upon review and study of the Drawings and the Detailed Description of the Invention which follow.

DETAILED DISCUSSION OF THE INVENTION

Embodiments of the present invention feature methods, devices and apparatus which will be described in detail with respect to the Figures in the context of chromatographic separations. Those skilled in the art of separations will understand that the invention has broad application and should not be limited to the precise details herein.

Figure 1:
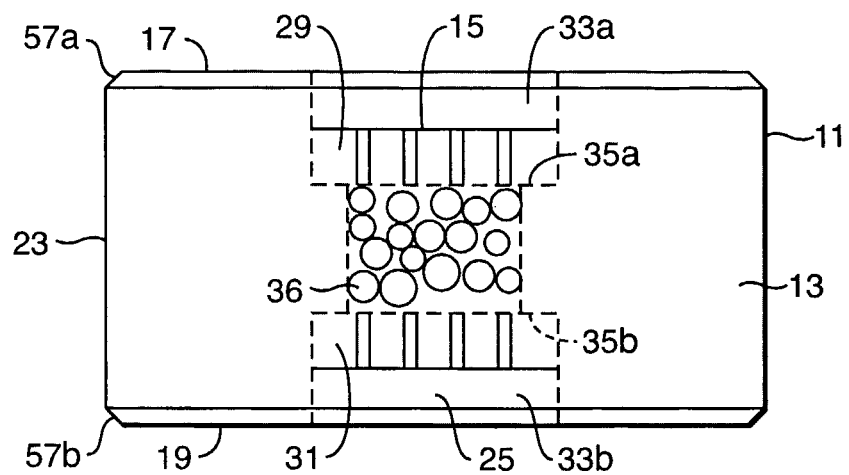
FIG. 1 depicts, in cross-section, a device embodying features of the present invention.

One embodiment of the present invention is a device for performing one or more separations, generally designated by numeral 11, as depicted in cross section in FIG. 1. Device 11 has the following major elements: a body 13 and a solid phase separation media assembly 15.

The body 13 has a first surface 17 and a second surface 19 and at least one wall 23. The designation of first and second being arbitrary as the device is substantially symmetrical. At least one of the first surface 17 and second surface 19 are capable of receiving in sealing engagement a conduit means [not shown]. The remaining first surface or second surface is capable of engaging a column or a second conduit means [not shown]. The wall 23 extends between said first surface 17 and the second surface 19. Conduit means may comprise any sort of conduit, piping, tubing and the like.

The body 13 has at least one opening 25 extending from the first surface 17 to the second surface 19 defining a chamber for receiving the solid phase separation media assembly 15. Opening 25 has a diameter and is constructed to correspond with the anticipated use with a analytical column [not shown]. Analytical columns have an interior diameter as understood by individuals skilled in the art. The diameter of the opening 25 is preferably sixty to eighty percent of the interior diameter of the analytical column with which the device 11 will be used. Normal opening 25 size is approximately 0.025 to 0.1 inches.

The solid phase separation media assembly 15 is held within the chamber formed by the opening 25 of the body 13. The solid phase separation media assembly 15 is for removing particulates and undesired components of a fluid flowing through the opening 25 and dampening the effect of pressure pulsation. The solid phase media assembly 15 may take several forms. The solid phase media assemble 15 may comprise a monolith porous structure as taught by Nakanichi et al in U.S. Pat. Nos. 5,009,688 and 5,624,875 and Frechet et al U.S. Pat. Nos. 5,334,310 and 5,453,185. Monoliths are known in the art and comprise organic, silica, and combinations thereof. A typical monolith has a thickness of 0.2 to 3.0 millimeters.

Figure 2:
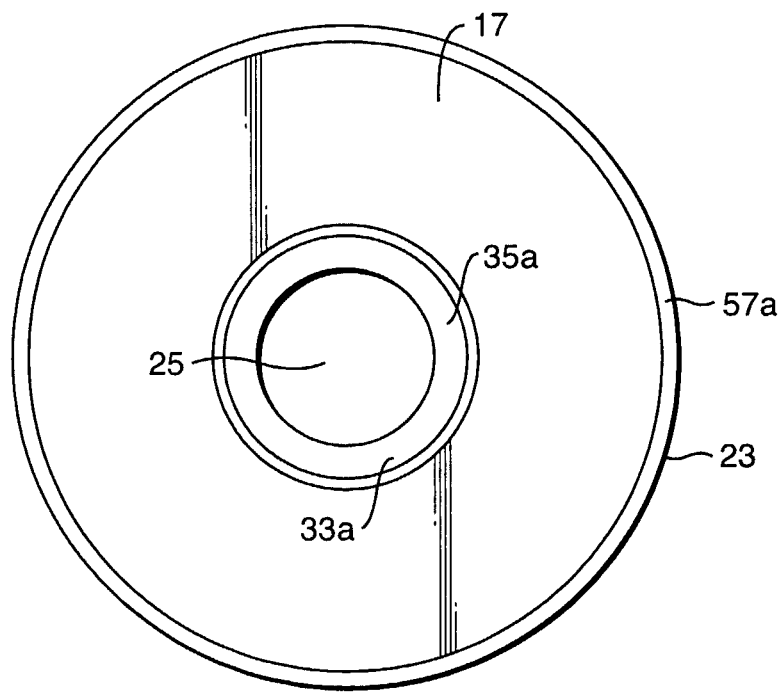
FIG. 2 depicts, in top view, a device embodying features of the present invention.

In the alternative, as depicted, the solid phase separation assembly 15 comprises a first frit 29 and a second frit 31. The body 11 has at least one a frit cavity and preferably two frit cavities 33a and 33b. Each frit cavity 33a and 33b is a depression or hollow in a first surface 17 and second surface 19 at opening 25 for receiving and affixing frit. As best seen in FIGS. 1 and 2, each frit cavity 33a and 33b has a frit abutment ridge 35a and 35b to facilitate assembly and affixing the first frit 29 and the second frit 31 by press fitting.

As a further alternative, the solid phase separation assembly 15 comprises a stacking of frits [not shown] in opening 25 between the first surface 17 and the second surface 19.

Returning now to FIG. 1, the first frit 29 is fixed to the opening 25 proximal to first surface 17 of the body 13. Similarly, the second frit 31 is fixed to the opening 25 proximal to the second surface 19 creating a chamber containing packing in the form of particles 36. The first frit 29 and the second frit 31 have a porosity of 0.5 microns. The first frit 29, second frit 31 and the particles 36 are permeable to fluids. A typical packing of particles 36 has a thickness in a range of 0.2 to 3.0 millimeters.

The particles 36 have a average diameter of 1 to 5 microns. The particles 36 may be organic polymers or inorganic solids known in the art.

Figure 3:
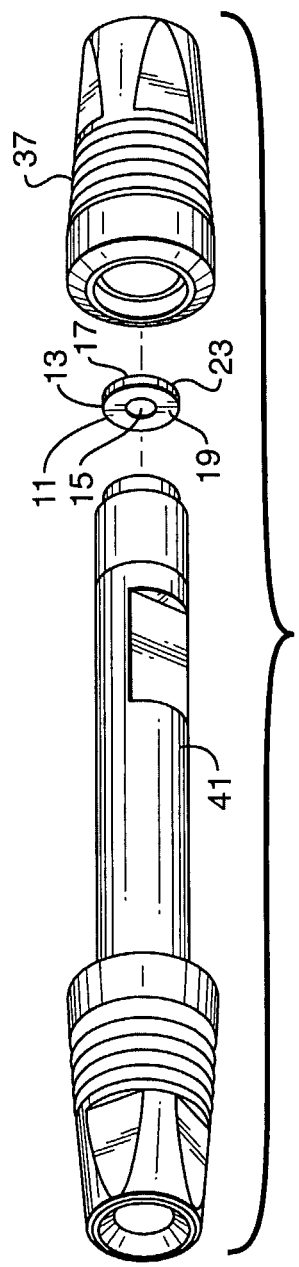
FIG. 3 depicts a device embodying features of the present invention.
Figure 8:
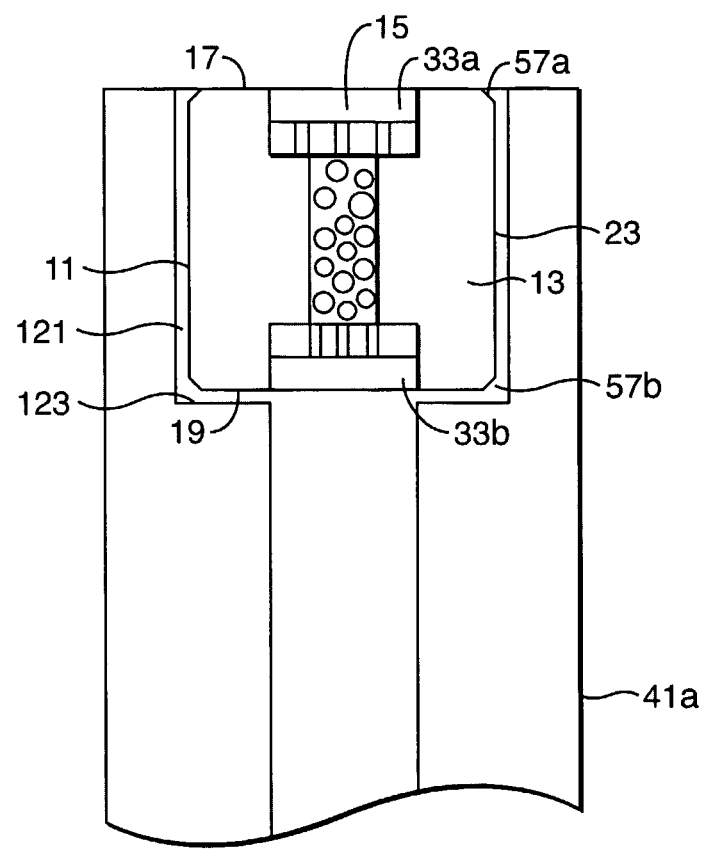
FIG. 8 depicts a column embodying features of the present invention.

Turning now to FIG. 3, the body 13 is constructed and arranged to fit in a body fitting 37, and now to FIG. 8, or the body 13 is constructed and arranged to fit inside a column 41. Returning now to FIG. 3, body fitting 27 is shown in expanded view apart from an analytical column 41 to which it is intended to be attached. Body fitting 37 may be used with other parts as part of an assembly for communicating with a column, as will be described later in this paper. Wall 23 of the body 13 is cylindrical and has an external diameter. The external diameter is approximately equal to the diameter of an analytical column. The diameters of normal and conventional analytical columns are in a range of approximately 0.5 to 4.0 mm.

The solid phase separation media assembly 15 of device 11 separates particulates and undesired components of a fluid prior to such fluid entering a second solid phase media assembly [not shown] of the analytical column 41 or other instrument components located downstream.

At least one of the first surface 17 and second surface 19, and, preferably, both, is capable of deforming in sealing engagement with connectors and columns, such as analytical column 41. Preferred materials for the body 11 include high strength plastics, steel, brass, iron, aluminum and mixtures and combinations thereof. A preferred material is steel in which the first surface 17 and the second surface 19 are annealed or softened to facilitate sealing.

Figure 4:
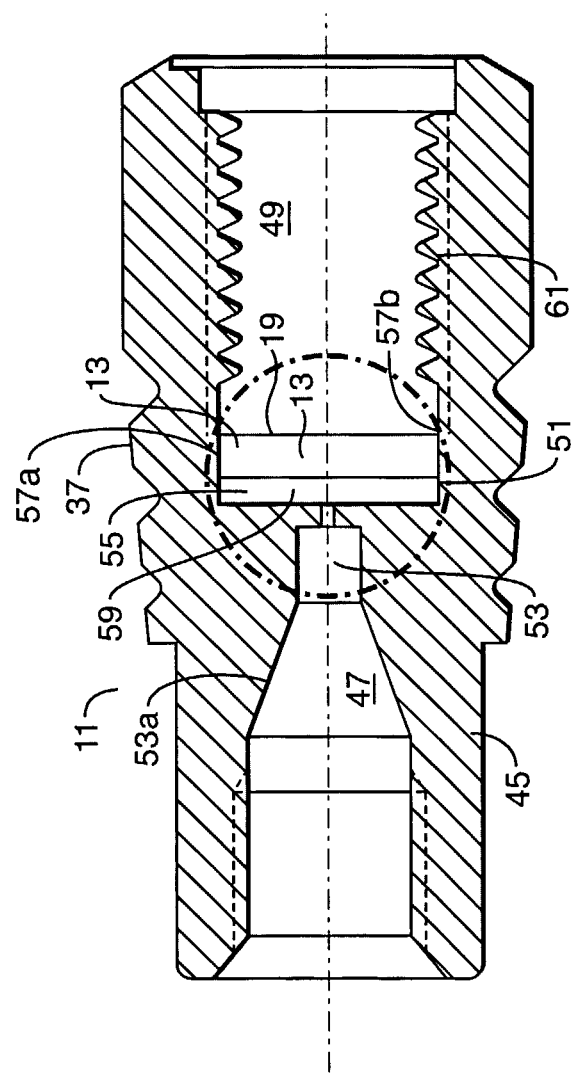
FIG. 4 depicts a fitting embodying features of the present invention.

Turning now to FIG. 4, body fitting 37 has a housing 45 having a passage 47. The passage 47 has an expanded portion 49, fitting abutment surface 51 and a narrow portion 53 and body manifold end wall 55. The expanded portion 47 receives the body 13 against the fitting abutment surface 51. The fitting abutment surface 51 sealing engages the first surface 17 or second surface 19 to which it is adjacent. The first surface 17 and second surface 19 have body rims 57a and 57b as best seen in FIG. 1. Body rims 57a and 57b are contoured to cooperate with fitting abutment surface 51.

The manifold end wall 55 separates the narrow portion 53 from the expanded portion 49 of passage 47. The area between manifold end wall 55 and first surface 17 of body 13 forms a manifold chamber 59 for distributing fluid into the opening 25 of the body 13.

Figure 5:
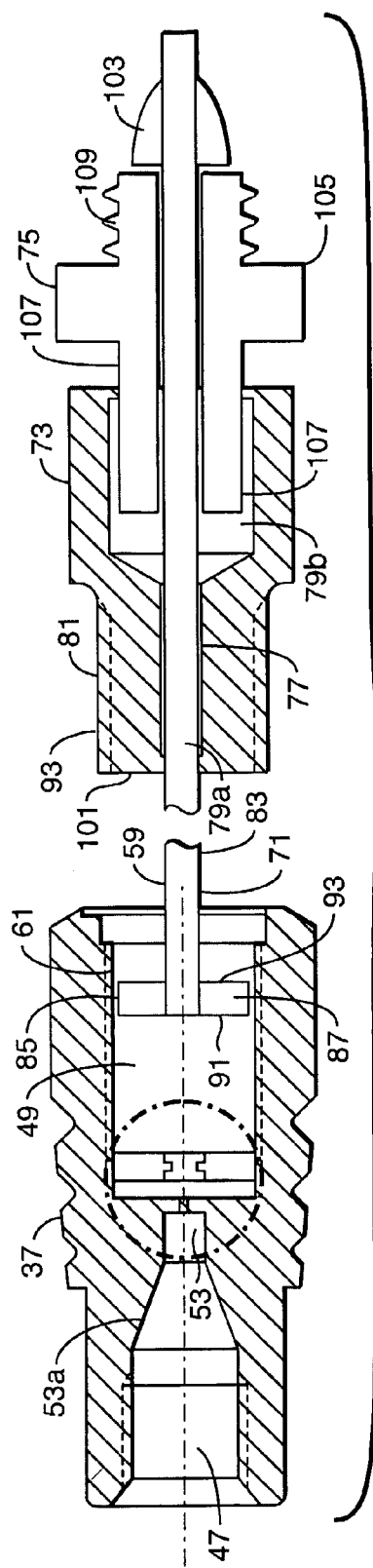
FIG. 5 depicts, in cross-section, a device embodying features of the present invention.

The expanded portion 49 of passage 47 receives at least one of the ends of a column 41, as best seen in FIG. 3, or a connector, such as a connecting assembly 59, as best seen in FIG. 5. As best seen in FIG. 3, the body fitting 37 has means for affixing, in sealing engaging the second surface 19 to such columns or connecting assemblies in the form of cooperating body fitting threads 61.

Figure 6:
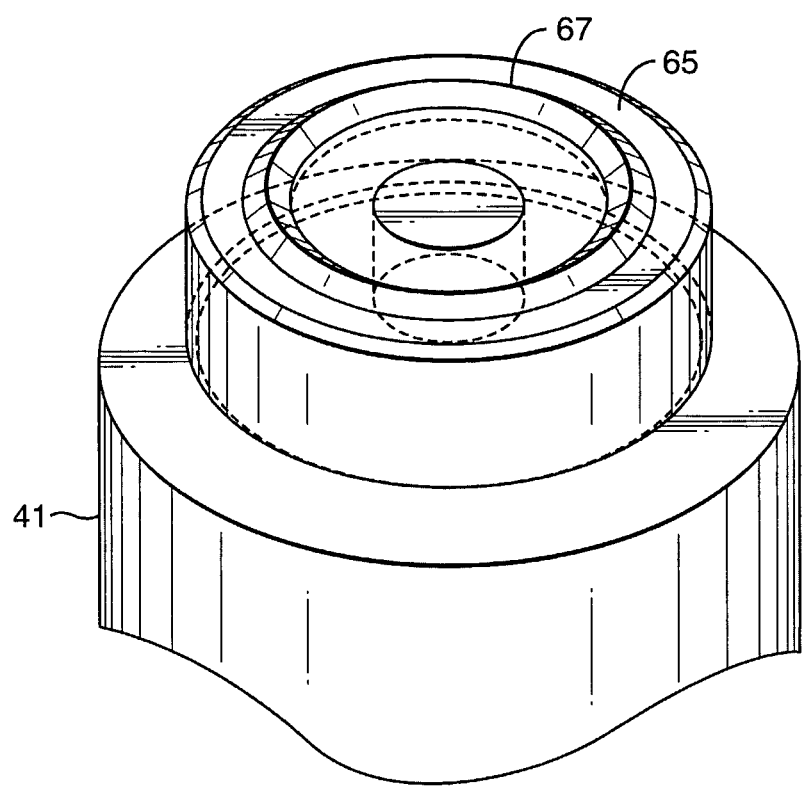
FIG. 6 depicts an end of a column embodying features of the present invention.

The body fitting threads 61 cooperate with corresponding cooperating threads [not shown] on column 41 or connector assembly 59, best seen in FIG. 5. Turning now to FIG. 6, one end of analytical column 41 is depicted. Analytical column 41 has a column terminal surface 65 for sealing engaging the first surface 17 or second surface 19 positioned in abutting relationship. Column terminal surface 65 has a ring projection 67 for focusing compressive forces against such first surface 17 or second surface 19 to facilitate sealing engagement.

In the alternative, the body fitting 37 and body 13 receive a connecting assembly 59 as best seen in FIG. 5. Connecting assembly 59 has the following elements: a tube connector 71, compression sleeve 73 and ferrule assembly 75.

Figure 7:
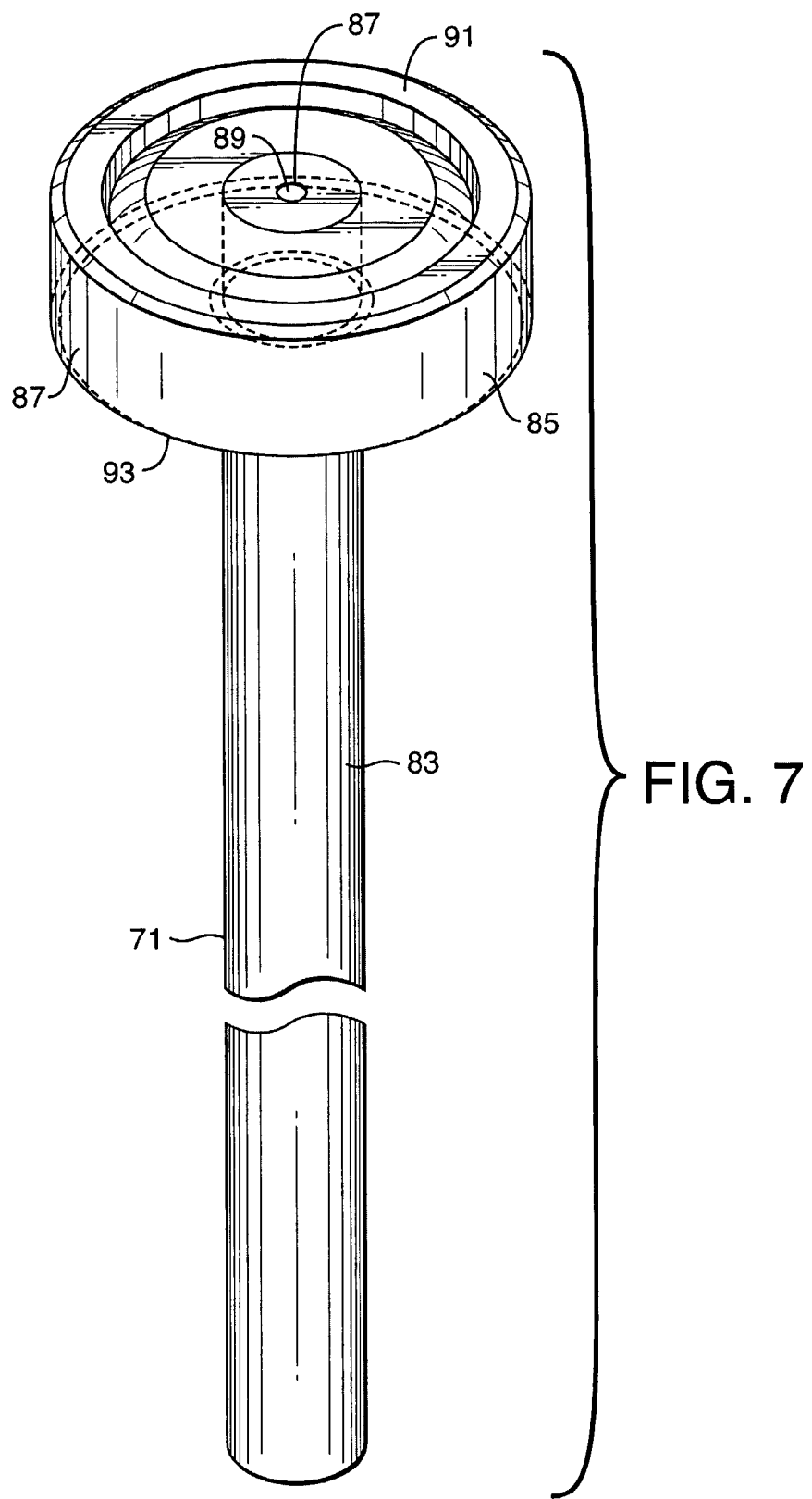
FIG. 7 depicts a tube connector embodying features of the present invention.

Turning now to FIGS. 5 and 7, tube connector 71 has a tubular section 83 and an abutment section 85. Tubular section 83 has an axial channel 89 for transporting fluids. Abutment section 85 is affixed to the tubular section 83 for securing and sealing the tubular connector to the first surface 17 or second surface 19 of body 13 to which it is adjacent to. Thus, abutment section 85 is received into the expanded portion 49 of passage 47 of body fitting housing 45.

Abutment section 85 is cylindrical with a diameter which is approximately equal to that of body 13. The abutment section 85 has a cylindrical wall 87, a first end focus compression for sealing engagement with the first surface 17 or second surface 19 of body 13 to which the first end wall is adjacent.

The compression sleeve 73 has an axial sleeve opening 77 having a narrow bore section 79a and a large bore section 79b. The narrow section 79a is for receiving tube section 83 of the tube connector 71. The large bore section 79b is for receiving parts of the ferrule assembly 75. The large bore section 79b allows for a more compact design which decreases the path fluid. Band spreading is associated with longer fluid paths.

The compression sleeve 73 has an outer threaded area 93 which cooperates with corresponding threads 61 on the body fitting 37. Those skilled in the art will recognize that other securing means may be substituted for cooperating threads such as cams, clamps and similar devices. Compression sleeve 73 has an abutment end wall 101 which is received against second end wall 93 of the tubular connector 59. The threaded area 93 and body fitting threaded area 61 allow the compression sleeve 73 to force abutment end wall 101 against the abutment section 85 to sealing engage the body 13 with the body fitting abutment surface 51 and the first end wall 91 of the tubular connector.

Ferrule assembly 75 is received on the tubular section 83 of tubular connector 71. Ferrule assembly 75 comprises a ferrule 103 and ferrule compression fitting 105. Ferrule 103 has a frusto-conical shape with an axial hole. Upon compression, the ferrule 103 compresses against the tubular section 31 in sealing engagement. The outer conical walls of the ferrule 103 sealing engages a cooperating wall of a connecting member [not shown] in a manner known in the art.

The ferrule compression fitting 105 has a first axle support section 107 and an affixing section 109. The axle support section 107 is received in the large bore area 79b of compression sleeve 73. The axle support section 107 is capable of substantially free rotation allowing the part of the device 11 to be rotate and secured to each other by threads which may have opposite directions or different ranges of rotation. The axle damage during the tightening operation.

Affixing section 109 has threads for cooperation with threads on a further fitting. This further fitting is not illustrated; however, such fitting would have features exemplified in the narrow portion 53 of the body fitting 37.

The narrow portion 53 is for receiving a source of fluid such as a conduit [not shown] and transporting the fluid into or out of said body 13. Preferably, the narrow portion receives a conduit by a ferrule connector assembly [not shown]. The narrow portion 53 has a frusto conical section 53a for receiving a ferrule [not shown] and means for affixing the body fitting to a conduit such as cooperating threads which receive a ferrule fitting [not shown]. Those skilled in the art will readily recognize that other means of affixing the ferrule to the body fitting 37 include clamps, cam devices and the like.

To facilitate tightening the body fitting 37, compression sleeve 73 and compression fitting 105 with respect to each other, such fittings, preferably, have nut-like exterior surfaces [not shown] to allow handling with wrenches and pliers.

In the alternative, returning again to FIG. 8, the body 13 is received inside an analytical column 41a. The analytical column 41a has a body hollow 121 for receiving the body 13. The body hollow 121 is an area at the end of the column 41a which is machined to the diameter of the body 13. The hollow 121 has a body receiving surface 123 for engaging one of the first surface 17 or second surface 19.

The device 11 of the present invention is capable of receiving fluids are under pressure, indeed, pressures greater than 4000 psi up to and including 15,000 psi.

Figure 9:
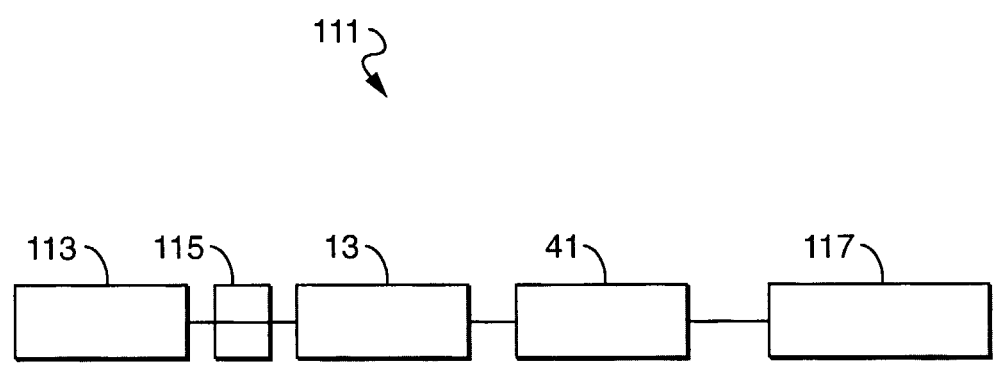
FIG. 9 depicts in block diagram an apparatus embodying features of the present invention.

In operation, the body 13 is used in a method of removing particulates and interfering materials from a fluid stream and dampening the effects of pressure pulsation. The method comprises the steps of placing a body 13 in the fluid stream. invention is depicted in block diagram form in FIG. 9. The apparatus 111 comprises a pump 113, means for placing a sample in a fluid stream 115, a column 41, body 13 and a detector 117.

Pump 113 is for moving fluids to create a fluid stream in a conduit. The conduit is depicted by solid lines extending between the described elements. Means for placing a sample into the fluid stream, such as a sample injector is in fluid communication with the pump. A body 13 having features as described earlier in this discussion is in fluid communication with the sample injector to receive the sample. Preferably, the body 13 is held in a body fitting 37 as described above. A column 41 is plumbed downstream of the body 13. The column 41 is for performing separations. The body 13 removes particulates and undesired components of the fluid flowing through the column 41 to extend the useful life of the column and to make separations performed with the column more reproducible.

These and other features and advantages will be apparent to those skilled in the art as well as modifications and changes to the teaching herein. Thus, the present invention should not be limited to the precise details herein but should encompass such subject matter as set forth in the claims.

What is claimed:

1. A device for performing one or more separations comprising:
   a.) a cylindrical body having a cylindrical axis and a pair of end walls each perpendicular to said cylindrical axis, said cylindrical body having a side wall concentric with said cylindrical axis, said end walls and said side wall comprising surfaces of an integral body, wherein each of said end walls is deformable to receive in sealing engagement a conduit or a column, said cylindrical body having an opening extending between said end walls concentric with said cylindrical axis and a counterbore at each of said end walls that is concentric with said opening; and
   b.) a solid phase separation media assembly disposed in said opening and counterbores to remove particulates and undesired components of a fluid flowing through said cylindrical body, wherein an entirety of said side wall of said cylindrical body is configured to fit in a body fitting to be attached to an analytical column or is part of an assembly for communicating with a column, wherein the solid phase separation media assembly comprises a frit positioned in each of the counterbores below the surfaces of the end walls.

2. The device of claim 1 wherein said opening has a diameter and said analytical column has a diameter said diameter of said opening is sixty to eighty percent of the diameter of said analytical column.

3. The device of claim 2 wherein said diameter of said opening is approximately 0.025 to 0.1 inches.

4. The device of claim 1 wherein said solid phase separation assembly is a monolith.

5. The device of claim 4 wherein said monolith has a thickness in a range of 0.2 to 3.0 millimeters.

6. The device of claim 1 wherein said solid phase separation media assembly includes at least one first frit, at least one second frit and a packing of particles of separation material, said first frit fixed to said opening proximal to said first surface of said integral body, said second frit fixed to said opening proximal to said second surface, said packing in said opening between said first frit and said second frit, to create a chamber containing particles which is permeable to fluids.

7. The device of claim 6 wherein said packing of particles has a thickness in a range of 0.2 to 3.0 millimeters.

8. The device of claim 6 wherein said particles have an average diameter of 1 to 5 microns.

9. The device of claim 6 wherein at least one of said first frit and second frit have a porosity of 0.5 microns.

10. The device of claim 1 wherein said side wall of said integral body is cylindrical and has an external diameter approximately equal to the diameter of an analytical column.

11. The device of claim 1 wherein at least one of said first surface and second surface is capable of deforming in sealing engagement with connectors and columns.

12. The device of claim 1 wherein said side wall of said integral body is cylindrical and has a diameter approximately 0.5 to 4.0 mm.

13. The device of claim 1 wherein said integral body is made from a material selected from the group comprising plastic, steel, brass, iron, and mixtures thereof.

14. The device of claim 1 wherein at least one of said end walls is softened to facilitate sealing.

15. The device of claim 1 further comprising a body fitting, said body fitting having attachment means for sealing engaging at least one of said end walls to a connecting means or column.

16. The device of claim 15 wherein said attachment means comprise threads which cooperate with threads on columns or connecting means.

17. The device of claim 16 further comprising a column.

18. The device of claim 17 wherein said column has an abutment surface for sealing engaging at least one of said end walls of said integral body.

19. The device of claim 18 wherein said abutment surface has a ring projection for focusing compressive forces against at least one of said end walls of said integral body.

20. The device of claim 15 wherein said body fitting has a passage, said passage having an expanded portion, fitting abutment surface and a narrow portion, said expanded portion for receiving said integral body and said fitting abutment surface for sealing engaging at least one of said end walls, and said narrow portion for receiving a source of fluid and transporting said fluid into or out of said integral body.

21. The device of claim 20 wherein said expanded portion is capable of receiving at least one of the ends of a column and a connector.

22. The device of claim 20 wherein said narrow portion has means for receiving a compression fitting.

23. The device of claim 20 wherein said body fitting has a hollow having a cylindrical wall, for receiving said cylindrical body.

24. The device of claim 23 wherein said cylindrical wall of said hollow has means for affixing said fitting to at least one of a column and connector.

25. The device of claim 24 wherein said means for affixing said body fitting to at least one of a column and a connector is cooperating threads.

26. The device of claim 23 wherein said connector is a tube connector having a fluid channel for placing said integral body in fluid communication.

27. The device of claim 26 wherein said tube connector has a fluid channel, tubular section and a terminal abutment section, said fluid channel extending through said tubular section and said terminal abutment section for sealing engagement with said end walls of said integral body to place said chamber of said integral body in fluid communication.

28. The device of claim 27 wherein said terminal abutment section has a cylindrical form received within the cylindrical wall of said hollow for receiving in sealing engagement at least one of said end walls of said integral body.

29. The device of claim 28 wherein said cylindrical form has an end wall having a planar surface with a ridge to focus compression forces.

30. The device of claim 27 wherein said hollow is capable of receiving a compression sleeve for placing said tube connector in fluid communication.

31. The device of claim 30 wherein said tube connector further comprises a ferrule assembly, said ferrule assembly comprising a ferrule fitted to the tubular section and a ferrule compression fitting.

32. The device of claim 31 wherein said ferrule compression fitting has an axle support section and said compression sleeve has a large bore area, said axle support area received in a large bore area to support the tubular member during tightening.

33. The device of claim 30 wherein said ferrule compression fitting has affixing means for attachment to further columns or connectors.

34. The device of claim 33 wherein said affixing means is cooperating threads.

35. The device of claim 1 wherein said fluids are under pressure of greater than about 4,000 pounds per square inch.

36. An apparatus for performing separations comprising:
a. a pump for moving fluids to create a fluid stream;
b. a column for performing separations in fluid communication with said pump to receive said fluid stream;
c. means for placing a sample in said fluid stream to allow said column to separate compounds in said sample as said sample flows through said column;
d. a cylindrical body having a cylindrical axis and a pair of end walls each perpendicular to said cylindrical axis, said cylindrical body having a side wall concentric with said cylindrical axis, said end walls and said side wall comprising surfaces of an integral body, wherein each of said end walls is deformable to receive in sealing engagement a conduit or a column conduit, said cylindrical body having an opening extending between said end walls concentric with said cylindrical axis and a counterbore at each of said end walls that is concentric with said opening, and a solid phase separation media assembly disposed in said opening and counterbores to remove particulates and undesired components of a fluid flowing through said cylindrical body, wherein an entirety of said side wall of said cylindrical body is configured to fit in a body fitting to be attached to an analytical column or is part of an assembly for communicating with a column;
e. a body fitting affixed to said column or interposed in said fluid stream, between said means for placing sample in said fluid stream and said column to extend the operational lifetime of said column; and
f. a frit positioned in each of the counterbores below the surfaces of the end walls.

37. The device of claim 1 wherein said integral body is received within a column.

38. The device of claim 1, wherein each frit is in direct contact with the counterbore in which the frit is disposed.

* * * * *